US012656329B2

(12) United States Patent
Nour et al.

(10) Patent No.: US 12,656,329 B2
(45) Date of Patent: Jun. 16, 2026

(54) POLYMER FILM FUEL DETECTOR

(71) Applicants: Saudi Arabian Oil Company, Dhahran (SA); King Abdullah University of Science and Technology, Thuwal (SA)

(72) Inventors: Maha Nour, Thuwal (SA); Esraa Fakeih, Thuwal (SA); Sumana Bhattacharjee, Thuwal (SA); Khaled Nabil Salama, Thuwal (SA); Abdullah Hassan Bukhamsin, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 483 days.

(21) Appl. No.: 18/301,610

(22) Filed: Apr. 17, 2023

(65) Prior Publication Data

US 2024/0345064 A1     Oct. 17, 2024

(51) Int. Cl.
   *G01N 33/28*     (2006.01)
   *G01N 33/22*     (2006.01)

(52) U.S. Cl.
   CPC ..... *G01N 33/2888* (2013.01); *G01N 33/2829* (2013.01); *G01N 33/2835* (2013.01)

(58) Field of Classification Search
   CPC .............. G01N 33/28; G01N 33/2829; G01N 33/2835; G01N 33/2841; G01N 2013/006
   See application file for complete search history.

(56) References Cited

U.S. PATENT DOCUMENTS

| | | | | |
|---|---|---|---|---|
| 4,434,233 | A | 2/1984 | Bzdula et al. | |
| 4,829,839 | A * | 5/1989 | Fisher | G01N 3/14 |
| | | | | 73/866 |
| 5,665,844 | A * | 9/1997 | Prass | G01N 21/553 |
| | | | | 526/309 |
| 8,643,388 | B2 * | 2/2014 | Hedges | G01N 33/2888 |
| | | | | 324/698 |
| 2017/0254791 | A1 * | 9/2017 | Nink | G01N 13/00 |
| 2021/0389264 | A1 | 12/2021 | Ito et al. | |
| 2022/0155328 | A1 | 5/2022 | Sliz et al. | |
| 2024/0328980 | A1 | 10/2024 | Nour et al. | |
| 2024/0329030 | A1 | 10/2024 | Nour et al. | |
| 2024/0345026 | A1 | 10/2024 | Nour et al. | |
| 2024/0345060 | A1 | 10/2024 | Nour et al. | |

(Continued)

FOREIGN PATENT DOCUMENTS

| | | | | |
|---|---|---|---|---|
| BR | PI1103900 A2 * | 12/2015 | ......... | G01N 33/2835 |
| CN | 111504850 A | 8/2020 | | |
| WO | WO-2017213419 A1 * | 12/2017 | ............. | G01N 21/41 |

OTHER PUBLICATIONS

Agha et al., "A Review of Cyclic Olefin Copolymer Applications in Microfluidics and Microdevices," Macromolecular Materials and Engineering, 2022, 307(2200053):1-34, 35 pages.

(Continued)

*Primary Examiner* — Herbert K Roberts
(74) *Attorney, Agent, or Firm* — Dinsmore & Shohl LLP

(57) ABSTRACT

A system and method for detecting aromatic compounds mixed with aliphatic compounds are provided. An exemplary system includes a lower substrate including a test magnet, a polymer film including a film magnet, and an upper substrate disposed over the polymer film, wherein the upper substrate includes an opening extending to the polymer film.

24 Claims, 5 Drawing Sheets

(56)                    References Cited

U.S. PATENT DOCUMENTS

2024/0345061 A1    10/2024  Kharashi et al.
2024/0345063 A1    10/2024  Kharashi et al.

OTHER PUBLICATIONS

COC Topas Product Brochure, Section 4.2; Table 2, Mar. 2006, 20 pages.
Ghosh et al., "A mass manufacturable thermoplastic based microfluidic droplet generator on cyclic olefin copolymer," J. Micromechanics Microengineering, Apr. 10, 2019, 29(5):055009, 9 pages.
Jain et al., "Design and Simulation of Microfluidic Passive Mixer With Geometric Variation," Int. J. Res. Eng. Technol., Feb. 2016, 5(2):55-58, 4 pages.
Jena et al., "Cyclic olefin copolymer based microfluidic devices for biochip applications: Ultraviolet surface grafting using 2-methacryloyloxyethyl phosphorylcholine," Biomicrofluidics, Mar. 2012, 6(1):012822-1-012822-12, 12 pages.
Jena et al., "Micro fabrication of cyclic olefin copolymer (COC) based microfluidic devices," Microsystem Technologies, Oct. 18, 2011, 18(2):159-166, 8 pages.
Kimmich et al., "Fault detection for modern Diesel engines using signal- and process model-based methods," Control Eng. Pract., Feb. 2005, 13(2):189-203, 15 pages.
Li et al., "Isoelectric focusing in cyclic olefin copolymer microfluidic channels coated by polyacrylamide using a UV photografting method," Electrophoresis, May 2005, 26(9):1800-1806, 7 pages.
McGann et al., "Lean fuel detection with nanosecond-gated laser-induced breakdown spectroscopy," Combustion and Flame, Feb. 2021, 224:209-218, 10 pages.
McGuire et al., "Detection of the aromatic molecule benzonitrile (c-C6H5CN) in the interstellar medium," Science, Jan. 12, 2018, 359(6372):202-205, 4 pages.
Nunes et al., "Cyclic olefin polymers: emerging materials for lab-on-a-chip Applications, " Microfluid Nanofluid, Apr. 2010, 9:145-161, 17 pages.
Taghizadeh-Alisaraei et al., "Fault detection of injectors in diesel engines using vibration time-frequency analysis," Applied Acoustics, Jan. 1, 2019, 143:48-58, 11 pages.

* cited by examiner

POLYMER FILM FUEL DETECTOR

TECHNICAL FIELD

This disclosure relates to a system and method for detecting hydrocarbon fuels blended in paraffin-based lubricants.

BACKGROUND

Fuel smuggling is a growing problem in international commerce. To avoid detection, smugglers may blend hydrocarbon fuels with lubrication oils and greases that are based on paraffinic compounds. Generally, hydrocarbon fuels contain low molecular weight aromatic compounds that can be used to detect the illicit compounds.

SUMMARY

An embodiment described herein provides a system for detecting aromatic compounds mixed with aliphatic compounds. The system includes a lower substrate including a test magnet, a polymer film including a film magnet, and an upper substrate disposed over the polymer film, wherein the upper substrate includes an opening extending to the polymer film.

Another embodiment described herein provides a method for detecting aromatic compounds mixed with aliphatic compounds. The method includes placing a sample of a test fluid on a polymer film through an opening in an upper substrate, wherein the polymer film is under stress from a film magnet and a test magnet in a lower substrate below the polymer film. A timer is started when the sample contacts the polymer film. The timer is stopped when the polymer film breaks, wherein a difference in time between starting the timer and stopping the timer provides a test time. The test time is used to determine if an aromatic compound is present in the test fluid.

DETAILED DESCRIPTION

Embodiments described herein provide a system and method for determining the presence of aromatic compounds in lubricants and greases based on paraffinic (aliphatic) compounds. The detection system, herein termed an aromatic detector, is based on the differential solubility of a polymer between aromatic compounds and aliphatic compounds.

A film is formed from a polymer, and then a film magnet is deposited in the center of the polymer film. In some embodiments, the film magnet is a magnetic polymer, for example, a polymer that has been blended with a magnetic powder before being deposited on the film. In other embodiments, the film magnet is a small spherical or pellet shaped magnet placed on the polymer film.

The polymer film and film magnet is placed over a test magnet mounted in a test apparatus. The attraction between the film magnet and the test magnet, as well as the weight of the film magnet, places the polymer film under stress. To test for aromatic compounds in a test fluid, a sample of the test fluid is placed on the polymer film, and if aromatic compounds are present, the polymer film will start to dissolve. The stress force caused by attraction between the film magnet and the test magnet will then break the film, indicating the presence of aromatic compounds in the test fluid.

For some polymers, contact with a material that is a poor solvent may result in stress cracking, or slower dissolution, leading to breaking of the polymer film under stress. However, the dissolution or disintegration rate will be faster for solvents, such as aromatic compounds. In these embodiments, the time to break the polymer film after the application of the test fluid can be compared to the time to break the polymer film after the application of a control fluid. For example, a paraffinic fluid or paraffinic oil that does not contain aromatics may be used as the control fluid.

Figure 1A:
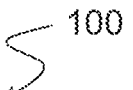
FIG. 1A is a perspective view of an aromatics detector based on a polymer film.
Figure 1A:
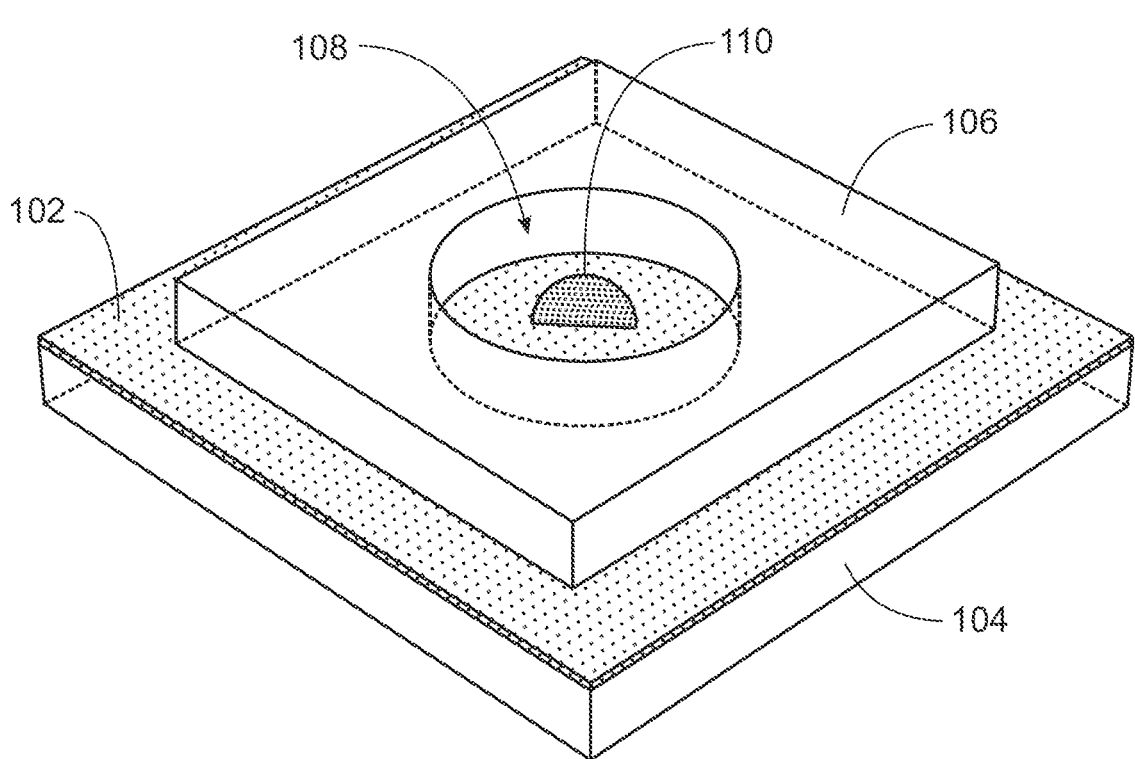
Figures 1B, 1C:
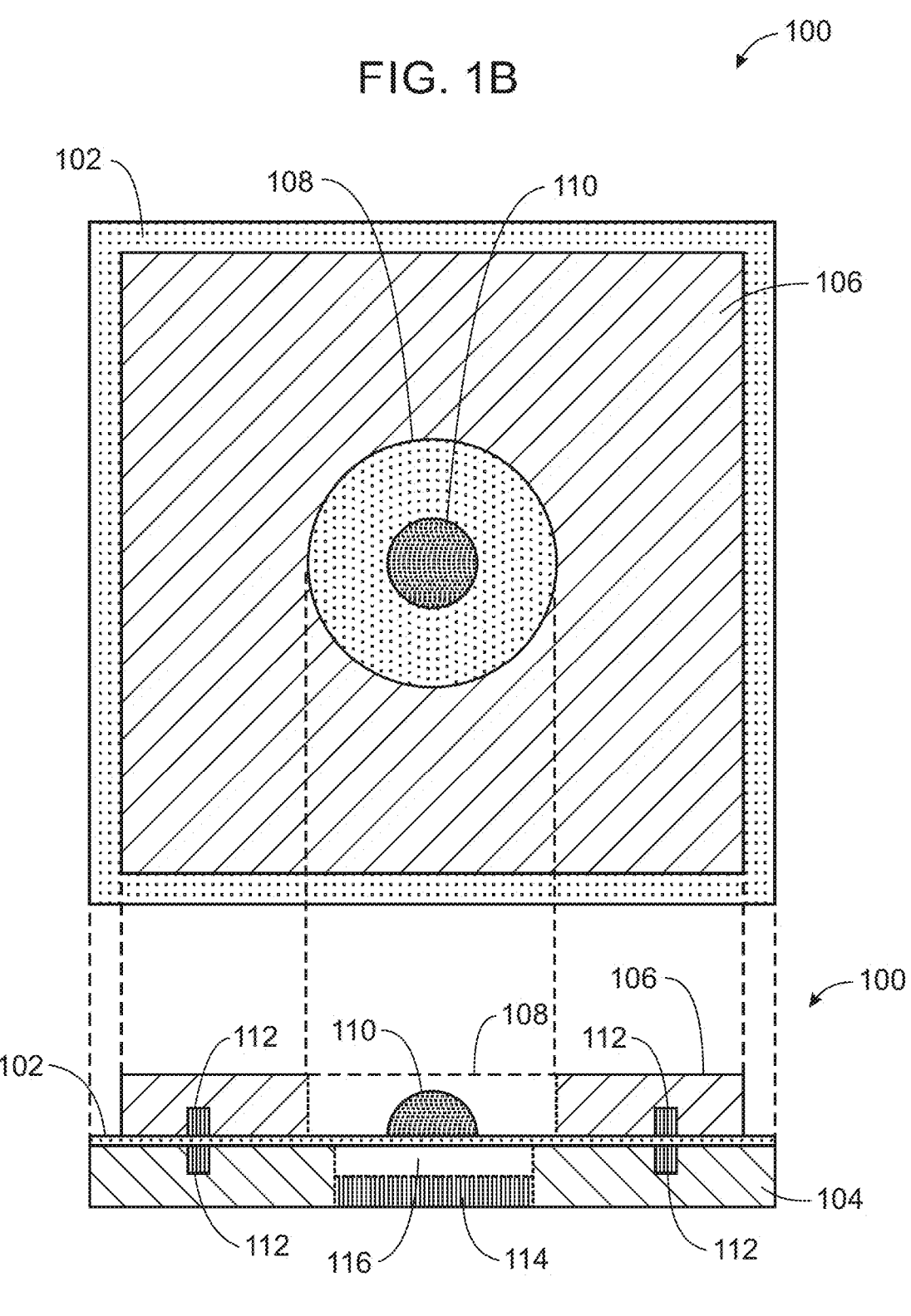
FIG. 1B is a top view of the aromatics detector.
FIG. 1C is a side, cross-sectional view of the aromatics detector.

The device, or aromatics detector, is discussed with respect to FIGS. 1A-1C. The polymer film and film magnet are discussed with respect to FIG. 2. A method for making the polymer film from a cyclic olefin copolymer (COC) is discussed with respect to FIG. 3. The test procedure for using the aromatics detector is discussed with respect to FIG. 4.

FIG. 1A is a perspective view of an aromatics detector 100 based on a polymer film 102. In the aromatics detector 100, the polymer film 102 is placed between a lower substrate 104 and an upper substrate 106. An opening 108 in the upper substrate 106 exposes the polymer film 102. The film magnet 110 is generally positioned in the center of the polymer film 102, for example, by forming a film magnet 110 from a magnetic polymer that is attached to the polymer film 102. If a separate film magnet 110, such as a magnetic bead, is used, then the attraction to the test magnet will generally center of the film magnet 110 on the polymer film 102. To center on the polymer film 102 through the opening 108.

To perform the test, a sample of a fluid is placed on the polymer film 102, for example, on or over the film magnet 110. The sample may be about 0.3 mL, about 0.5 mL, about 1 mL, or about 2 mL, or more. The amount of sample used may depend on the likely concentration of aromatics in the solution.

In various embodiments, the lower substrate 104 comprises polymethyl methacrylate, acetal copolymer, acetal homopolymer, nylon, polytetrafluoroethylene (PTFE), polyvinylidene fluoride copolymer, or glass, or any combinations thereof. In various embodiments, the upper substrate 106 comprises polymethyl methacrylate, acetal copolymer, acetal homopolymer, nylon, polytetrafluoroethylene (PTFE), polyvinylidene fluoride copolymer, or glass, or any combinations thereof. The lower substrate 104 and the upper substrate 106 may be made from different materials.

FIG. 1B is a top view of the aromatics detector 100. The top view shows the opening 108 through which the polymer film 102 is accessible. In this view, the film magnet 110 is shown in the center of the opening 108. As described herein, during a test, a sample of the test fluid is placed on the polymer film 102 through the opening 108.

FIG. 1C is a side, cross-sectional view of the aromatics detector 100. As can be seen in this view, the polymer film 102 is held in place between the lower substrate 104 and the upper substrate 106. In some embodiments, magnets 112 built into the lower substrate 104 and the upper substrate 106 are used to assist with alignment during assembly. In various embodiments, the lower substrate 104 and the upper substrate 106 are held together with mechanical clips, adhesives, or solvent bonding.

In some embodiments, a test magnet 114 is mounted in the lower substrate 104, for example, in an opening 116 located below the polymer film 102. The opening 116 ensures that the polymer film 102 is unsupported under the sample, creating stress on the polymer film 102 from the attraction between the film magnet 110 and the test magnet 114. The diameter of the test magnet 114 and the proximity to the polymer film 102 can be selected, for example, based on the polymer and the strength of the magnetic field between the film magnet 110 and the test magnet 114. In various embodiments, the test magnet 114 includes NdFeB, CoSm, and the like. Similar materials may be used for the magnets 112 used for alignment. The openings 108 and 116 can be fabricated using a $CO_2$ laser or a mechanical process.

As materials, such as aromatic compounds, attack the polymer film 102, it will fail under the stress from the film magnet 110 and test magnet 112. As discussed below, the time to failure can be used to indicate the presence of the aromatic compounds from fuels.

Figure 2:
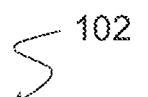
FIG. 2 is a drawing of a polymer film having a polymer and a film magnet includes magnetic particles.
Figure 2:
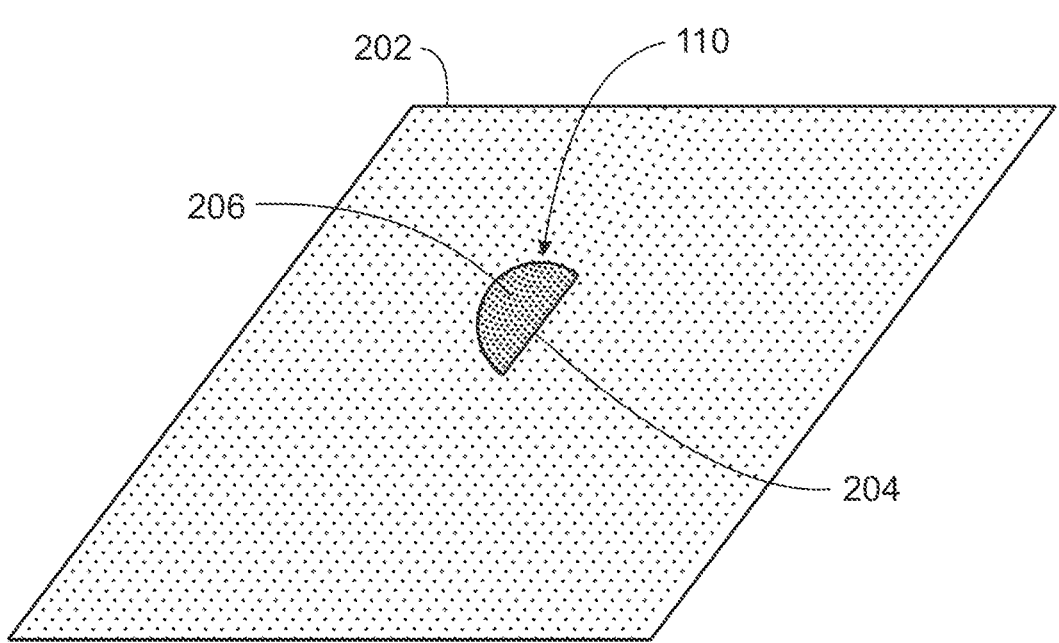

FIG. 2 is a drawing of a polymer film 102 having a polymer 202 and a film magnet 110 that includes magnetic particles. In various embodiments, the polymer 202 is a cyclic olefin copolymer (COC), a poly (acrylonitrile butadiene styrene) (ABS), a polyphenylene oxide (PPO), and the like. The choice of the polymer 202 may be used to control the sensitivity of the test, depending on the susceptibility of the polymer 202 to dissolution or stress cracking from components of the sample.

As described herein, the film magnet 110 may be a magnetic polymer or a small permanent magnet, such as a magnetic bead. The magnetic polymer includes a polymer matrix 204 with embedded magnetic particles 206. The polymer matrix 204 may be the same or a different polymer as used for the polymer film 202. The polymer matrix 204 does not need to be susceptible to attack by aromatic compounds, as the test sample is able to attack the polymer film 102 around the film magnet. In some embodiments, the polymer matrix 204 is polydimethylsiloxane (PDMS), and the like.

Figure 3:
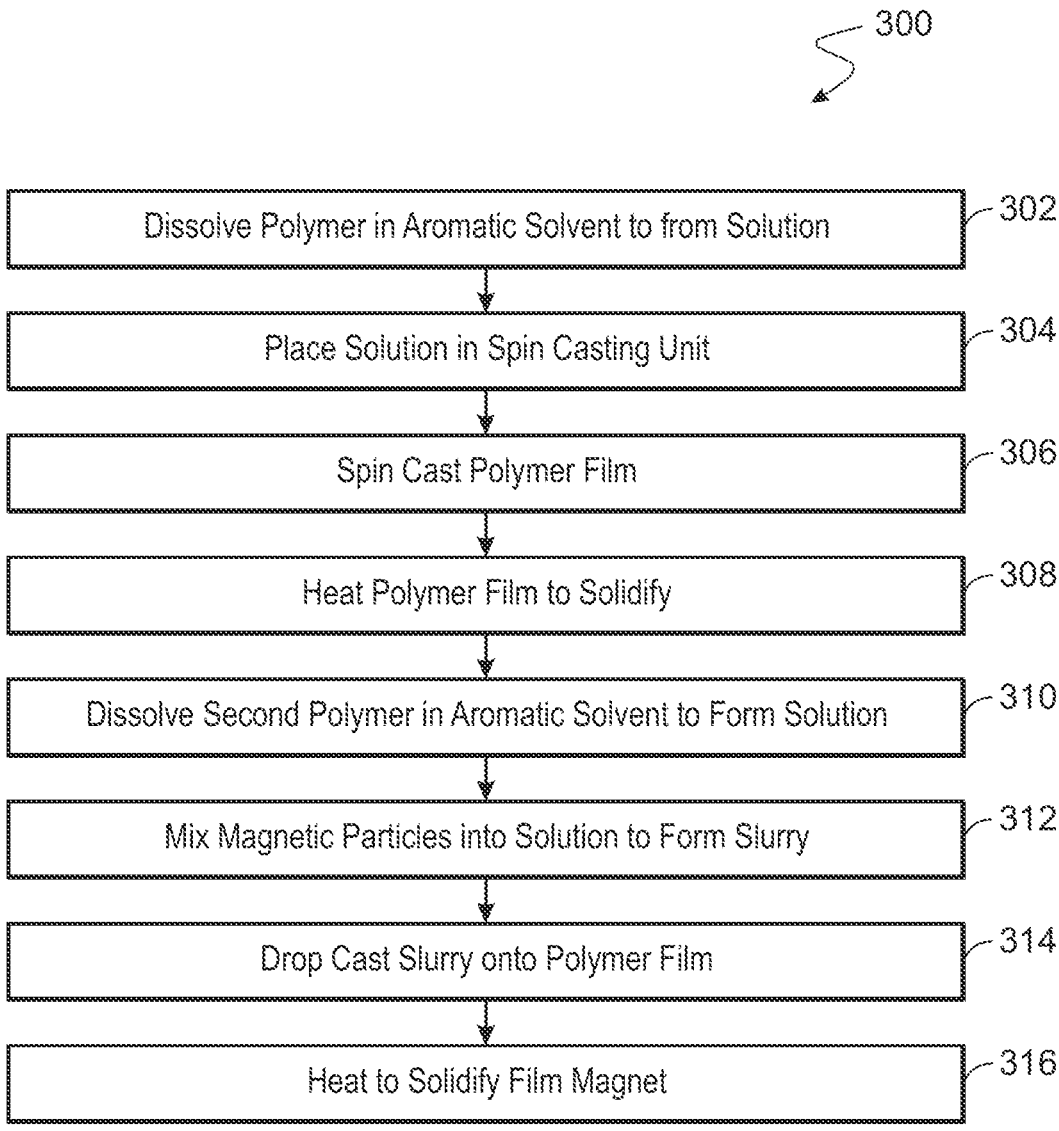
FIG. 3 is a method of making a polymer film from a cyclic olefin copolymer (COC).

In various embodiments, the magnetic particles 206 include neodymium-iron-boron (NdFeB), magnetite (($Fe^{2+}$ $Fe^{3+})_2O_4$), iron (Fe), cobalt, nickel, and the like. The choice of the magnetic particles 206 may also be used to control the sensitivity, as particles made from stronger magnetic materials may increase the stress on the polymer film, for example, NdFeB may be stronger than iron, which may be stronger than magnetite. Further, the size of the magnetic particles 206 may be selected based on the thickness of the polymer film 102 expected. In various embodiments, the magnetic particles 206 may be less than about 200 nm in size, less than about 500 nm in size, less than about 1000 nm in size, or less than about 5000 nm in size. Larger particles may be used in thicker films, for example, made from more susceptible polymers FIG. 3 is a method 300 of making a polymer film from a cyclic olefin copolymer (COC). At block 302, the COC is dissolved in toluene to form a solution. At block 304, the solution is placed in the spin-casting unit, for example, being injected through a syringe onto a spinning substrate. At block 306, the polymer film is spin cast as the solution is flowed onto a rotating platform. The rotation speed and the concentration of the COC in the solvent controls the thickness of the COC layer. For example, the concentration of the COC in the toluene solvent may range from about 10% to about 30%, or about 20%. The rotational speed of the spin-casting unit can be about 500 to about 5000 rpm, or about 1000 rpm to about 4000 rpm, or about 2000 rpm. At block 308, the solvent is then evaporated through a baking process that decreases the evaporation time, forming a solid polymer film from the solution.

At block 310, a second polymer is dissolved in an aromatic solvent to form a solution. At block 312, the solution is mixed with the magnetic powder, such as NdFeB, to form a slurry. At block 314, the slurry is drop cast onto the polymer film.

At block 316, the solvent is then evaporated through a baking process that decreases the evaporation time, forming the film magnet from the solution. The film magnet is then magnetized, for example, in an electromagnetic field. The orientation of the magnetic field may be selected based on the magnetic field of the test magnet 114 (FIG. 1).

In some embodiments, the polymer film is formed by plastics processing techniques. For example, pellets of the polymer selected are used to form a film, for example, in a sheet extruder or a blown film extruder. The film is then cut into the final size and shape, for example, as shown with respect to FIGS. 1A-1C, and FIG. 2.

The film magnet may then be formed and drop cast onto the polymer film, as described with respect to blocks 310-316. As described herein, the film magnet may be a permanent magnet placed on the polymer film.

Figure 4:
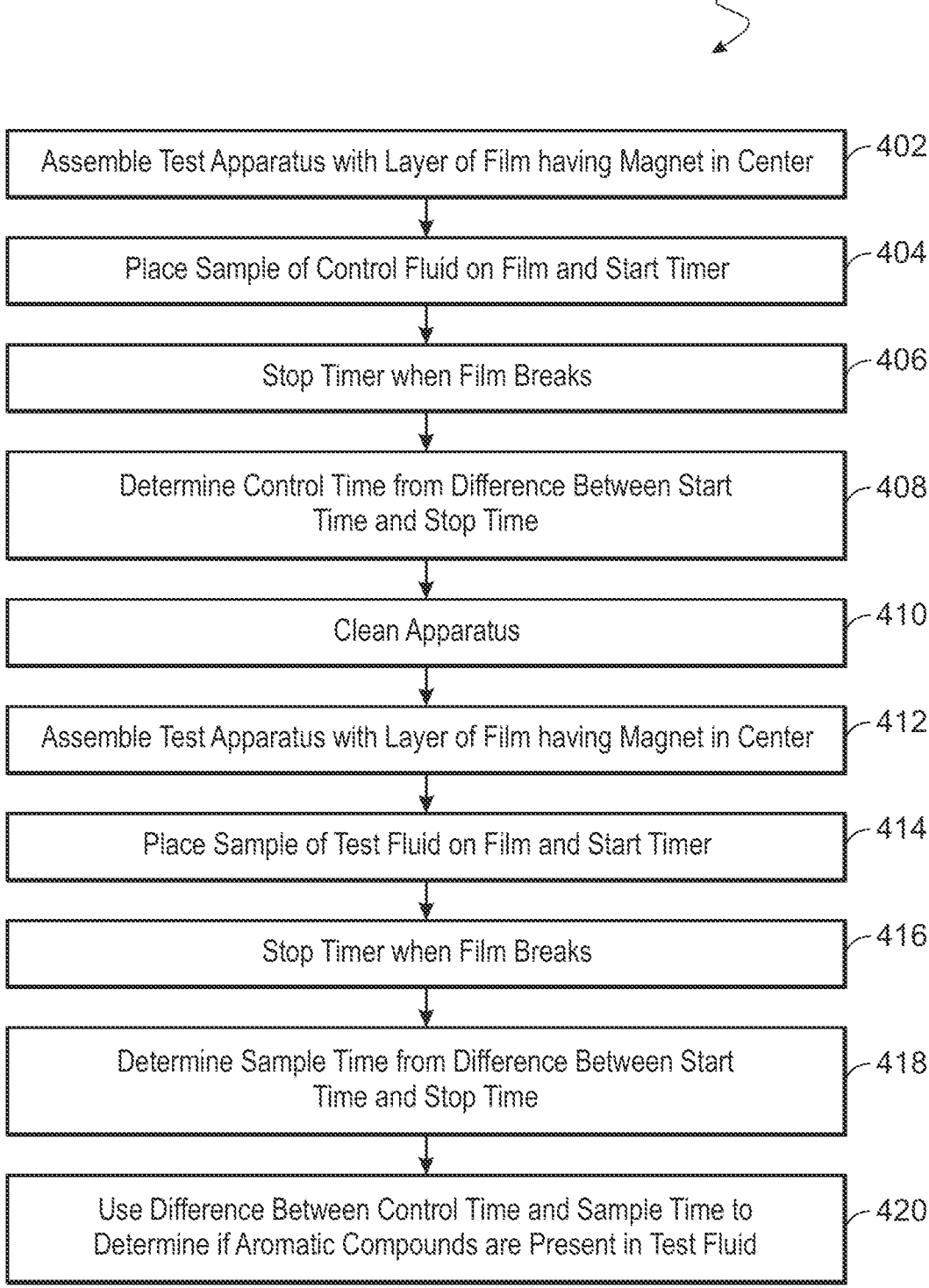
FIG. 4 is a method of using an aromatics detector to determine the presence of aromatics mixed into a matrix of aliphatic compounds.

FIG. 4 is a method 400 of using an aromatics detector to determine the presence of aromatics mixed into a matrix of aliphatic compounds. The method begins at block 402 with assembling a test apparatus that includes a polymer film, as described herein. The test apparatus is assembled by placing the polymer film between two substrates. A lower substrate, placed under the polymer film, includes a magnet to place the polymer film under stress by attraction between the film magnet and the test magnet. An upper substrate, placed over the polymer film, has an opening leading to the polymer film. If the film magnet is a permanent magnet, such as a magnetic bead, it is placed on the polymer film through the opening, and is held in place by the test magnet.

At block 404, a sample of a control fluid is placed on the polymer film, for example, around or over the film magnet, and a timer is started. At block 406, the timer is stopped when the polymer film breaks. At block 408, the time for the control fluid to break the polymer film, or the control time, is calculated by taking the time difference between the starting time and the stopping time of the timer.

At block 410, the apparatus is cleaned. For example, the upper substrate is separated from the lower substrate and the broken polymer film is removed. Any excess control fluid is wiped away or removed by cleaning. In some embodiments, the test apparatus is a one-time use apparatus, and is discarded after the test is complete. In these embodiments, a single determination of the control time may be made and supplied with the test apparatus.

At block 412, the test apparatus is reassembled with a fresh layer of polymer film, having a magnet at the center. At block 414, a sample of test fluid is placed on the polymer film and the timer is started. At block 416, the timer is stopped when the polymer film breaks. At block 418, the time for the test fluid to break the polymer film, or the test time, is calculated by taking the time difference between the starting time and the stopping time of the timer.

At block 420, a difference between the control time and the sample time is used to determine if aromatic compounds are present in the test fluid, indicating the contamination of the paraffinic compounds. For example, the sample time will be lower than the control time, as the polymer is more susceptible to dissolution or stress cracking from aromatic compounds than from aliphatic compounds.

The test procedure is not limited to the specific steps shown in the blocks above. For example, if the polymer used is not susceptible to dissolution by aliphatic compounds, the test may be implemented with no control fluid. In this example, a few milliliters of the test sample is placed on the polymer film through the opening of the upper substrate, and the leakage of the liquid through the polymer film is observed visually.

EXAMPLES

Forming the COC Film

The formation of a COC film was tested. The COC was purchased from TOPAS advanced polymers of Florence, KY, USA. The great selected was 50131-10 which had 3 mm nominal granule size.

A COC solution was first made using 30% (w/w) of COC crystals dissolved in Toluene. The solution was then spin coated at a speed of 1500 rpm for 30 sec and then heated on a hot plate of 40° C. to dry the COC thin film. The film was then released from the carrier wafer.

Design with Glass Substrate

Initially, the COC film was affixed to a glass substrate for support. Acrylic frame was cut to attach on top of the glass-COC-gold stack, to act as holder for the drop casted diesel.

Design with Released COC Thin Film

To achieve this, the COC thin film was released from the substrate using acetone. The film was subsequently sputtered and diced to make samples for testing. The film was placed between two acrylic frames. An external film magnet can be placed on the film, or a drop cast magnetic film is cast on the film as the film magnet.

Embodiments

An embodiment described herein provides a system for detecting aromatic compounds mixed with aliphatic compounds. The system includes a lower substrate including a test magnet, a polymer film including a film magnet, and an upper substrate disposed over the polymer film, wherein the upper substrate includes an opening extending to the polymer film.

In an aspect, the opening is between the test magnet and the polymer film.

In an aspect, the lower substrate includes glass. In an aspect, the lower substrate includes acetal copolymer, acetal homopolymer, nylon, polytetrafluoroethylene (PTFE), or polyvinylidene fluoride, or any combination thereof.

In an aspect, the polymer film includes a cyclic olefin copolymer (COC). In an aspect, the polymer film includes poly (acrylonitrile butadiene styrene) (ABS). In an aspect, the polymer film includes polyphenylene oxide (PPO).

In an aspect, the film magnet includes a magnetic polymer including magnetic particles, and wherein the magnetic polymer is disposed on the polymer film. In an aspect, the magnetic polymer includes polydimethylsiloxane (PDMS). In an aspect, the magnetic particles include neodymium-iron-boron (NdFeB). In an aspect, the magnetic particles include magnetite ($(Fe^{2+}Fe^{3+})_2O_4$). In an aspect, the magnetic particles include iron (Fe).

In an aspect, the upper substrate includes glass. In an aspect, the upper substrate includes acetal copolymer, acetal homopolymer, nylon, polytetrafluoroethylene (PTFE), or polyvinylidene fluoride, or any combination thereof.

Another embodiment described herein provides a method for detecting aromatic compounds mixed with aliphatic compounds. The method includes placing a sample of a test fluid on a polymer film through an opening in an upper substrate, wherein the polymer film is under stress from a film magnet and a test magnet in a lower substrate below the polymer film. A timer is started when the sample contacts the polymer film. The timer is stopped when the polymer film breaks, wherein a difference in time between starting the timer and stopping the timer provides a test time. The test time is used to determine if an aromatic compound is present in the test fluid.

In an aspect, the method includes assembling a test apparatus with a layer of the polymer film between the upper substrate and the lower substrate.

In an aspect, the method includes removing the layer of the polymer film from the test apparatus once it breaks, cleaning the test apparatus, and reassembling the test apparatus with a new layer of polymer film between the upper substrate and the lower substrate. In an aspect, the method includes placing a sample of control fluid on the new layer of the polymer film through the opening in the upper substrate, starting the timer when the sample contacts the polymer film, stopping the timer when the polymer film breaks, and using the measured time from starting the timer to stopping the timer as a control time. In an aspect, the method includes comparing the test time to the control time to determine if the aromatic compound is present in the test fluid.

In an aspect, the method includes forming the polymer film by dissolving a polymer in an aromatic solvent to form a solution, placing the slurry in a spin casting unit, and casting the polymer film. In an aspect, the polymer includes a cyclic olefin copolymer. In an aspect, the magnetic particles include neodymium-iron-boron (NdFeB).

In an aspect, the method includes forming the polymer film by extruding the polymer into a film. In an aspect, the polymer includes and acrylonitrile butadiene styrene (ABS) copolymer.

Other implementations are also within the scope of the following claims.

What is claimed is:

1. A method for detecting aromatic compounds mixed with aliphatic compounds, comprising:
placing a sample of a test fluid on a polymer film through an opening in an upper substrate, wherein the polymer film is under stress from a film magnet and a test magnet in a lower substrate below the polymer film;
starting a timer when the sample contacts the polymer film;
stopping the timer when the polymer film breaks, wherein a difference in time between starting the timer and stopping the timer provides a test time; and
using the test time to determine if an aromatic compound is present in the test fluid.

2. The method of claim 1, comprising assembling a test apparatus with a layer of the polymer film between the upper substrate and the lower substrate.

3. The method of claim 2, comprising:
removing the layer of the polymer film from the test apparatus once it breaks;

cleaning the test apparatus; and reassembling the test apparatus with a new layer of polymer film between the upper substrate and the lower substrate.

4. The method of claim 3, comprising:

placing a sample of control fluid on the new layer of the polymer film through the opening in the upper substrate;

starting the timer when the sample contacts the polymer film;

stopping the timer when the polymer film breaks; and using a measured time from starting the timer to stopping the timer as a control time.

5. The method of claim 4, comprising comparing the test time to the control time to determine if the aromatic compound is present in the test fluid.

6. The method of claim 1, comprising forming the polymer film by:

dissolving a polymer in an aromatic solvent to form a solution;

mixing magnetic particles into the solution to form a slurry;

placing the slurry in a spin casting unit; and casting the polymer film.

7. The method of claim 6, wherein the polymer comprises a cyclic olefin copolymer.

8. The method of claim 6, wherein the magnetic particles comprise neodymium-iron-boron (NdFeB).

9. The method of claim 1, comprising forming the polymer film by:

compounding a filler comprising magnetic particles into a polymer; and extruding the polymer into a film.

10. The method of claim 9, wherein the polymer comprises an acrylonitrile butadiene styrene (ABS) copolymer.

11. The method of claim 2, comprising forming the polymer film by:

dissolving a polymer in an aromatic solvent to form a solution;

mixing magnetic particles into the solution to form a slurry;

placing the slurry in a spin casting unit; and casting the polymer film.

12. The method of claim 11, wherein the polymer comprises a cyclic olefin copolymer.

13. The method of claim 11, wherein the magnetic particles comprise neodymium-iron-boron (NdFeB).

14. The method of claim 2, comprising forming the polymer film by:

compounding a filler comprising magnetic particles into a polymer; and extruding the polymer into a film.

15. The method of claim 14, wherein the polymer comprises an acrylonitrile butadiene styrene (ABS) copolymer.

16. The method of claim 2, comprising forming the polymer film by:

compounding a filler comprising magnetic particles into a polymer; and extruding the polymer into a film.

17. The method of claim 16, wherein the polymer comprises an acrylonitrile butadiene styrene (ABS) copolymer.

18. The method of claim 1, wherein the sample is between 0.3 mL and 2 mL.

19. The method of claim 2, wherein the sample is between 0.3 mL and 2 mL.

20. The method of claim 11, wherein the sample is between 0.3 mL and 2 mL.

21. The method of claim 1, wherein the test magnet comprises neodymium-iron-boron (NdFeB) or samarium-cobalt (CoSm).

22. The method of claim 1, wherein the film magnet comprises a magnetic bead.

23. The method of 1, wherein the film magnet is positioned in a center of the polymer film.

24. The method of claim 1, wherein a diameter of the test magnet and a proximity to the polymer film are selected based on a polymer of the polymer film and a strength of a magnetic field between the film magnet and the test magnet.

* * * * *